Dec. 29, 1942. J. J. GRULLEMANS Plant Pat. 562

KNIPHOFIA OR TRITOMA

Filed Aug. 22, 1942

WITNESS

Addison E. Avery

INVENTOR

John J. Grullemans, by John Harrow Kennard, his attorney.

Patented Dec. 29, 1942

Plant Pat. 562

UNITED STATES PATENT OFFICE

562

KNIPHOFIA OR TRITOMA

John J. Grullemans, Painesville, Ohio, assignor to The Wayside Gardens Company, Mentor, Ohio, a corporation of Ohio Application August 22, 1942, Serial No. 455,741

1 Claim. (Cl. 47—60)

Figures 1, 2:
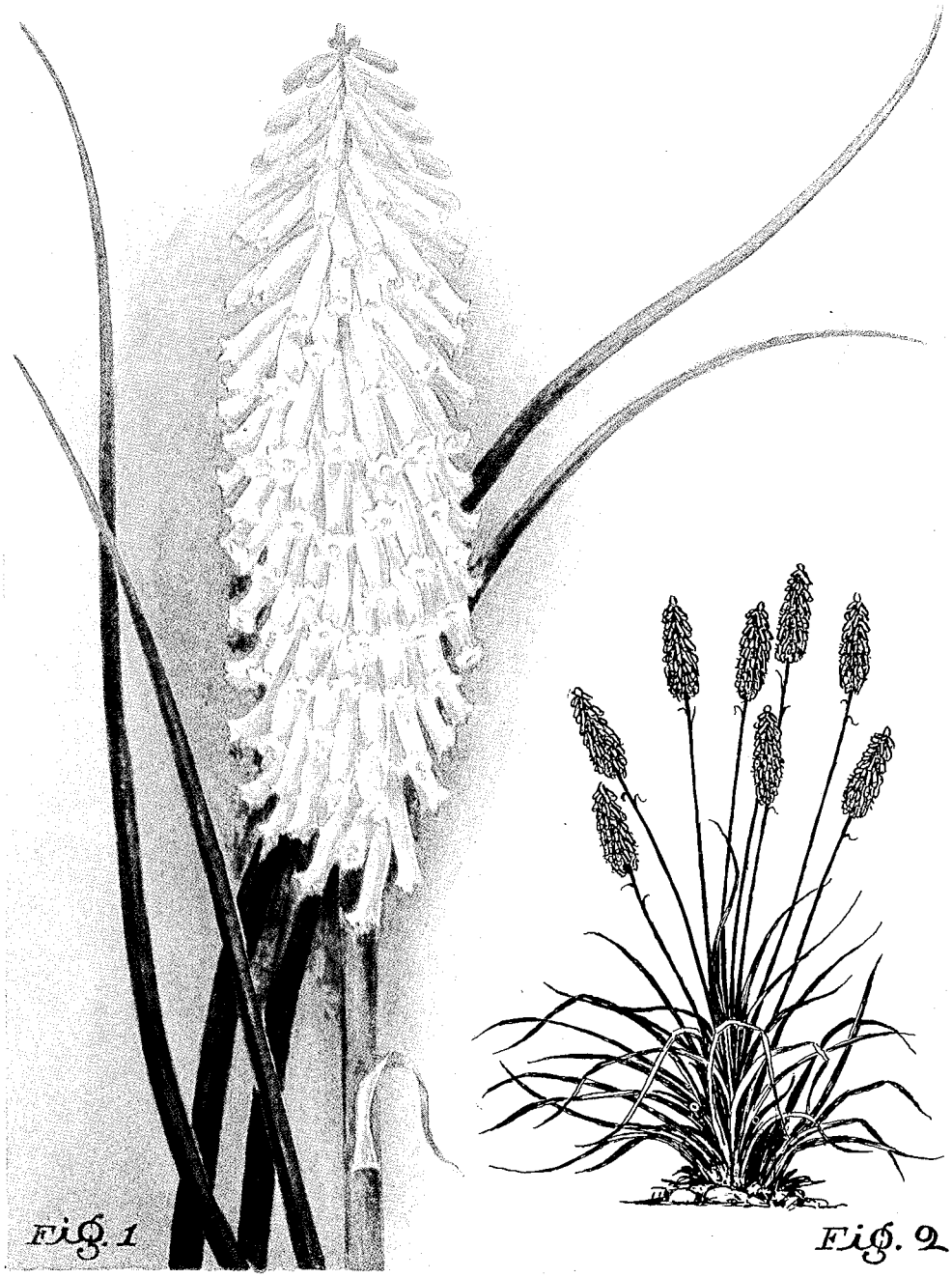

This invention relates to a new and distinct variety of Kniphofia, commonly termed Tritoma.

The present kniphofia variety is the result of the cross pollination of the species *Kniphofia rufa* and the variety *Kniphofia uvaria grandiflora*. Specimens of parent plants were crossed by planting them in contigous beds remote from other beds, the transfer of pollen by insects and wind and the favorable aspect of the law of probabilities resulting from the relative proximity of the specimens so planted being relied on to effect the cross pollination of the particular parents. These fertilized plants were allowed to produce seed which was permitted to fall in the bed and the bed was subsequently observed for desirable hybrid varieties.

One variety thus produced and discovered was the present Kniphofia variety. The plant was first produced and discovered about 1934 and was first asexually reproduced in 1938 in the fields of The Wayside Gardens Company at Mentor, Lake County, Ohio, where the original plant was produced. Asexual reproduction by division has been carried on continuously since the discovery and the plant has reproduced true to form consistently and has been reproduced in large numbers.

The plant is deep rooted, the roots being thin and clustered and of fleshy consistency. The roots are slightly smaller than those of the parents and are of very limited lateral spread. They are exceptionally hardy, free from disease, resistant to wetness, drouth, and winter weather. The roots have withstood the winters of northern Ohio without protection since the development of the plant. The plant is relatively indifferent as to soil but it prefers a southern exposure in the sun with well drained soil.

The new variety is illustrated in the drawing in which Fig. 1 shows, on a reduced scale, specimens of the stalks, flower spikes and leaves and Fig. 2 shows, on a more reduced scale, the plant as a whole.

The exposed portion of the plant is herbaceous, generally upright with dense and compact foliage, growing to about eighteen inches in height on the average and having a spread of about twelve inches, being slightly below average in size for Kniphofia. The growth is vigorous and the plant multiplies somewhat more rapidly than is usual.

A two year old plant has from five to ten clones or crowns, each of which, in season, produces a flower spike, whereas, ordinarily, a two year old Kniphofia plant produces only two to four clones, each having one spike, these crowns being somewhat larger and more bulky than those of the present variety. Each crown readily produces another multi-crowned plant each year or two, so that propagation and multiplication of the variety is relatively simple.

The leaves are abundant and have a tendency to droop at their termini. They are closely packed at the base of the plant. In color they are Spinach Green, comparable to Maerz and Paul Plate No. 22–K–7 on the upper surface and about the same color on the lower surface. The color is relatively uniform except near the base where it is comparable to Maerz and Paul Plates Nos. 13–K–4 and 5. The leaves are from .25 to .38 inch across and are from twelve to thirty inches long on a two year plant, most of them being nearer the upper limit of their length. They are slightly narrower and smaller than is usual for Kniphofia. The leaves are thick and relatively stiff toward the base of the plant but terminate in fairly long points. They have smooth upper surfaces and closely spaced minute teeth or spines along their margins. Near their bases the leaves are generally V-shaped in cross section, this cross section assuming more the shape of a three-pointed star progressively from the base toward the termini. The leaves persist excellently on the plant.

The flower stalks grow upright from the base and though they are of slightly smaller diameter than is usual, they are very tough and support the flower spike well and in upright position. They are strong enough to resist relatively heavy winds. They are from thirty-six to forty inches in length and are from .30 to .40 inch in diameter near the base, thus being of slightly smaller diameter than the flower stalks of most Kniphofiae. In color they are comparable to Maerz and Paul Plates Nos. 20–L–4 and 21–L–4, having areas near the base comparable to Maerz and Paul Plate 13–K–4. Both the leaves and flower stalks are exceedingly uniform for a given plant or for a number of plants of the same age under the same growing conditions.

The blooms are in the form of spikes of short pedicelled florets and are the usual shape except that they are somewhat larger.

For flowering conditions, sun with a southern exposure or a relatively hot, dry, well drained location are preferred although the plant flowers well in ordinary garden soil. The plant, however, does not survive in the shade.

The blooming period begins in late July and continues through the forepart of August. During this period, the plant blooms continuously.

The blooms persist well both as cut and uncut flowers.

The new buds are produced in relatively small spikes of generally conical or pyramidal shape which are borne upright on the stalks. Their color is green or white with a greenish tinge, comparable to Maerz and Paul Plates Nos. 17–J–3, 17–K–3 and 18–K–3, at the tip of the spike and at the upper part of the spike the color is comparable to Maerz and Paul Plate No. 17–H–1. When the buds are ready to bloom the color is white with a slight greenish tinge and is comparable to Maerz and Paul Plate No. 17–H–1 and 18–J–1.

The florets are white with a very slight greenish tinge and are comparable to Maerz and Paul Plate No. 17–F–1 and 17–D–1. The color of the pollen in a fully bloomed floret is comparable to Maerz and Paul Plate No. 9–L–3. The ends of the trumpet-like florets in this kniphofia are the same waxy consistency and appearance and the same color as the floret itself.

The florets forming the spike have very short pedicels which support the florets in a generally horizontal or downward sloping position forming a very compact, large and solid head or spike. The spikes begin blooming at the base and the blooming progresses very rapidly upwardly so that the spikes are in full bloom over the entire extent for most of the blooming period and persist in this condition for a long period. One spike is borne on each clone or crown so that on a two year old plant five to ten spikes are in bloom concurrently, even though the plant is fairly small and compact.

Though the stalks are relatively short for kniphofiae, their length varies with the richness of the soil and the moisture but they are very consistent for any given plant in a given location or group of plants of the same age in a given location.

The spikes on a two year old plant are from six and one half to seven inches long and a full two inches across at the point of largest diameter. The flower spikes are elongated and somewhat pointed at the end.

The exterior of the tubes and petals of each floret are generally comparable to Maerz and Paul Plate No. 17–F–1 and there appears to be no red in the color. This uniform whiteness throughout the length of the spike is most unusual. In fact, the present variety is believed to be the first kniphofia to have a spike which is entirely white.

The individual florets are trumpet-shaped with a tube about two tenths of an inch in diameter though tapering from about the longitudinal midportion toward the base. The diameter of the open end of a floret is about seven sixteenths of an inch and the florets are about one inch long. Each floret has very light yellow or yellowish green stamens, comparable to Maerz and Paul Plate No. 9–F–1 with yellow pollen, comparable to Maerz and Paul Plate No. 9–F–4.

These dimensions of the individual florets, the number of florets on a spike and consequent size of the spike, the consistency of color and size, both of spikes and florets on a given plant, the uniform length and size of stalks and the like are exceptional, the variations therein being so slight as to be negligible and unnoticeable for a given plant or group of plants of the same age under the same growing conditions.

The plant is sterile.

The characteristic which most distinguishes the plant from other Kniphofiae is the unusual color of the flower spike. Other outstanding qualities are its above average floriferousness, the flower spikes which are in bloom over their entire extent at the same time; the large size of the spikes; the general tonality of the spikes; and the good proportions of the spikes and of the spikes to the stalks.

Having now fully shown and described my new kniphofia, and the mode of its production, what I claim and desire to secure by Letters Patent of the United States is:

The variety of Kniphofia, or Tritoma, herein shown and described, characterized primarily by the unusual color of the florets and general tonality of the flower spikes, and further characterized by the uniformity of its growth and of its flower spikes in a given location; its manner of blooming, and the size and number of flower spikes on a given plant.

JOHN J. GRULLEMANS.